(12) United States Patent
Yellin et al.

(10) Patent No.: US 12,263,033 B2
(45) Date of Patent: Apr. 1, 2025

(54) HISTORICAL ULTRASOUND DATA FOR DISPLAY OF LIVE LOCATION DATA

(71) Applicant: Biosense Webster (Israel) Ltd., Yokneam (IL)

(72) Inventors: Tamir Avraham Yellin, Yokneam Hamoshava (IL); Natan Sharon Katz, Atlit (IL); Benjamin Cohen, Haifa (IL); Lior Zar, Poria Illit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 511 days.

(21) Appl. No.: 16/681,408

(22) Filed: Nov. 12, 2019

(65) Prior Publication Data

US 2021/0137488 A1  May 13, 2021

(51) Int. Cl.
*A61B 8/08* (2006.01)
*A61B 8/00* (2006.01)
(Continued)

(52) U.S. Cl.
CPC .............. *A61B 8/0841* (2013.01); *A61B 8/12* (2013.01); *A61B 8/13* (2013.01); *A61B 8/4263* (2013.01); *A61B 8/5207* (2013.01)

(58) Field of Classification Search
CPC ........... A61B 8/0841; A61B 8/12; A61B 8/13; A61B 8/4263; A61B 8/5207; A61B 8/145;
(Continued)

(56) References Cited

U.S. PATENT DOCUMENTS

| 5,542,915 A | 8/1996 | Edwards et al. |
| 6,045,508 A * | 4/2000 | Hossack ............. G01S 15/8915 |
| | | 600/463 |

(Continued)

FOREIGN PATENT DOCUMENTS

| JP | 2004-016268 A | 1/2004 |
| JP | 2007-503906 A | 3/2007 |
| JP | 2017-532131 A | 11/2017 |

OTHER PUBLICATIONS

Extended European Search Report dated Mar. 29, 2021 for European Patent Application No. 20206959.7.
(Continued)

*Primary Examiner* — Yi-Shan Yang
*Assistant Examiner* — Nicholas A Robinson
(74) *Attorney, Agent, or Firm* — Volpe Koenig

(57) ABSTRACT

Methods, apparatus, and systems for medical procedures include receiving a first ultrasound slice from an ultrasound transducer, the first ultrasound slice corresponding to a first ultrasound position. A second ultrasound slice is received from the ultrasound transducer, the second ultrasound slice corresponding to a second ultrasound position. The first ultrasound slice and the second ultrasound slice are stored in memory. A first catheter position of a catheter is received. The first catheter position is determined to correspond to the first ultrasound position and the first ultrasound slice is provided based on the determination. The determination that the first catheter position corresponds to the first ultrasound position may be made based on locations, orientations, or may be based on the number of voxels that overlap between the first catheter position and ultrasound positions.

13 Claims, 8 Drawing Sheets

(51) Int. Cl.
*A61B 8/12* (2006.01)
*A61B 8/13* (2006.01)

(58) Field of Classification Search
CPC ..... A61B 8/4245; A61B 8/5215; A61B 90/37; A61B 34/10; A61B 34/20
See application file for complete search history.

(56) References Cited

U.S. PATENT DOCUMENTS

| | | | |
|---|---|---|---|
| 6,138,495 A * | 10/2000 | Paltieli | A61B 17/3403 73/1.86 |
| 6,332,089 B1 * | 12/2001 | Acker | A61N 7/02 128/899 |
| 6,690,963 B2 * | 2/2004 | Ben-Haim | A61N 1/32 606/41 |
| 2002/0045810 A1 | 4/2002 | Ben-Haim | |
| 2003/0060700 A1 | 3/2003 | Solf et al. | |
| 2003/0220561 A1 | 11/2003 | Camus et al. | |
| 2005/0288586 A1 * | 12/2005 | Ferek-Petric | A61B 8/5238 600/443 |
| 2006/0074319 A1 * | 4/2006 | Barnes | A61B 5/06 600/466 |
| 2006/0253030 A1 | 11/2006 | Altmann et al. | |
| 2007/0049827 A1 * | 3/2007 | Donaldson | A61B 8/5238 600/443 |
| 2007/0106147 A1 * | 5/2007 | Altmann | A61B 8/12 600/407 |
| 2007/0265526 A1 * | 11/2007 | Govari | A61B 34/20 600/424 |
| 2010/0049034 A1 * | 2/2010 | Eck | A61B 6/12 600/437 |
| 2011/0230758 A1 | 9/2011 | Eichler | |
| 2012/0143055 A1 * | 6/2012 | Ng | A61B 8/0841 600/439 |
| 2013/0338477 A1 * | 12/2013 | Glossop | A61B 10/0241 600/407 |
| 2015/0182190 A1 | 7/2015 | Hiltner et al. | |
| 2015/0269728 A1 * | 9/2015 | Parthasarathy | G06T 7/0012 382/131 |
| 2018/0206825 A1 * | 7/2018 | Ziv-Ari | B29B 7/84 |
| 2018/0229053 A1 * | 8/2018 | Kruecker | A61N 5/1039 |
| 2019/0307516 A1 * | 10/2019 | Schotzko | A61B 8/0841 |

OTHER PUBLICATIONS

Japanese Office Action dated May 24, 2024 for Japanese Patent Application No. 2020-187832.

* cited by examiner

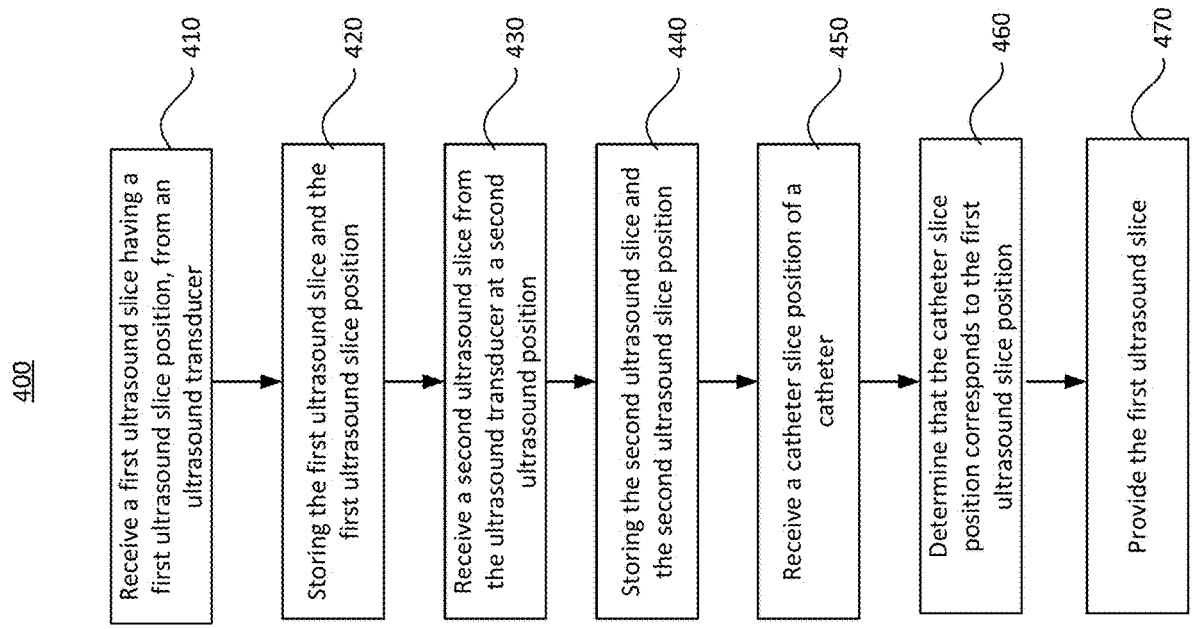

HISTORICAL ULTRASOUND DATA FOR DISPLAY OF LIVE LOCATION DATA

FIELD OF INVENTION

The present application provides systems, apparatuses, and methods for improving medical procedures.

BACKGROUND

Medical conditions such as cardiac arrhythmia (e.g., atrial fibrillation (AF)) are often diagnosed and treated via intra-body procedures. For example, electrical pulmonary vein isolation (PVI) from the left atrial (LA) body is performed using ablation for treating AF. Pulmonary vein isolation, and many other minimally invasive catheterizations, require real-time visualization and mapping of an intra-body surface.

Visualization of intra-body surfaces can be performed by mapping propagation of activation waves. Fluoroscopies, computerized tomography (CT) and magnetic resonance imaging (MRI), as well as other techniques may require a greater than desirable amount of time or resources to provide the visualization and mapping. Additionally, graphical renderings used to visualize intra-body surfaces may not include a sufficient amount of detail when compared to other modes of visualization.

SUMMARY

Methods, apparatus, and systems for medical procedures are disclosed herein include receiving a first ultrasound slice from an ultrasound transducer, the first ultrasound slice corresponding to a first ultrasound position. A second ultrasound slice is received from the ultrasound transducer, the second ultrasound slice corresponding to a second ultrasound position. The first ultrasound slice and the second ultrasound slice are stored in memory. A first catheter position of a catheter is received. The first catheter position is determined to correspond to the first ultrasound position and the first ultrasound slice is provided based on the determination. The determination that the first catheter position corresponds to the first ultrasound position may be made based on locations, orientations, or may be based on the number of voxels that overlap between the first catheter position and ultrasound positions.

BRIEF DESCRIPTION OF THE DRAWINGS

A more detailed understanding can be had from the following description, given by way of example in conjunction with the accompanying drawings wherein:

FIG. 4 is another flowchart for providing an ultrasound slice based on a catheter's position;

DETAILED DESCRIPTION

According to implementations of the disclosed subject matter, a previously captured ultrasound slice of an area of an organ may be displayed, based on a current location of a catheter.

A plurality of ultrasound slices may be captured and stored in memory. The plurality of ultrasound slices may be captured using an ultrasound transducer that traverses different portions of an organ and captures the plurality of ultrasound slices while the ultrasound transducer is in a plurality of corresponding ultrasound transducer positions. After capturing and storing the plurality of ultrasound slices using the ultrasound transducer, a catheter may be inserted into the organ. The catheter's position may be determined and may include a catheter location and a catheter orientation. Alternatively, the catheter's position may be determined and may be based on the voxels that may be occupied by an ultrasound slice if the catheter was an ultrasound transducer collecting the ultrasound slice from the catheter's position. To clarify, as disclosed herein, a live catheter's current position may be determined based on a catheter location and a catheter orientation or, alternatively, may be determined based on occupied voxels.

The catheter's position may be compared to the plurality of ultrasound positions which correspond to the plurality of ultrasound slices. A first ultrasound position may be determined to correspond to the catheter's position and the first ultrasound slice may be selected. The selected ultrasound slice may be provided for display. Notably, the selected ultrasound slice may show the area of the organ that corresponds to the catheter's present position such that a health care professional is able to visually see the area of the organ corresponding to the catheter's present position, by being provided the previously stored ultrasound slice.

Figure 1:
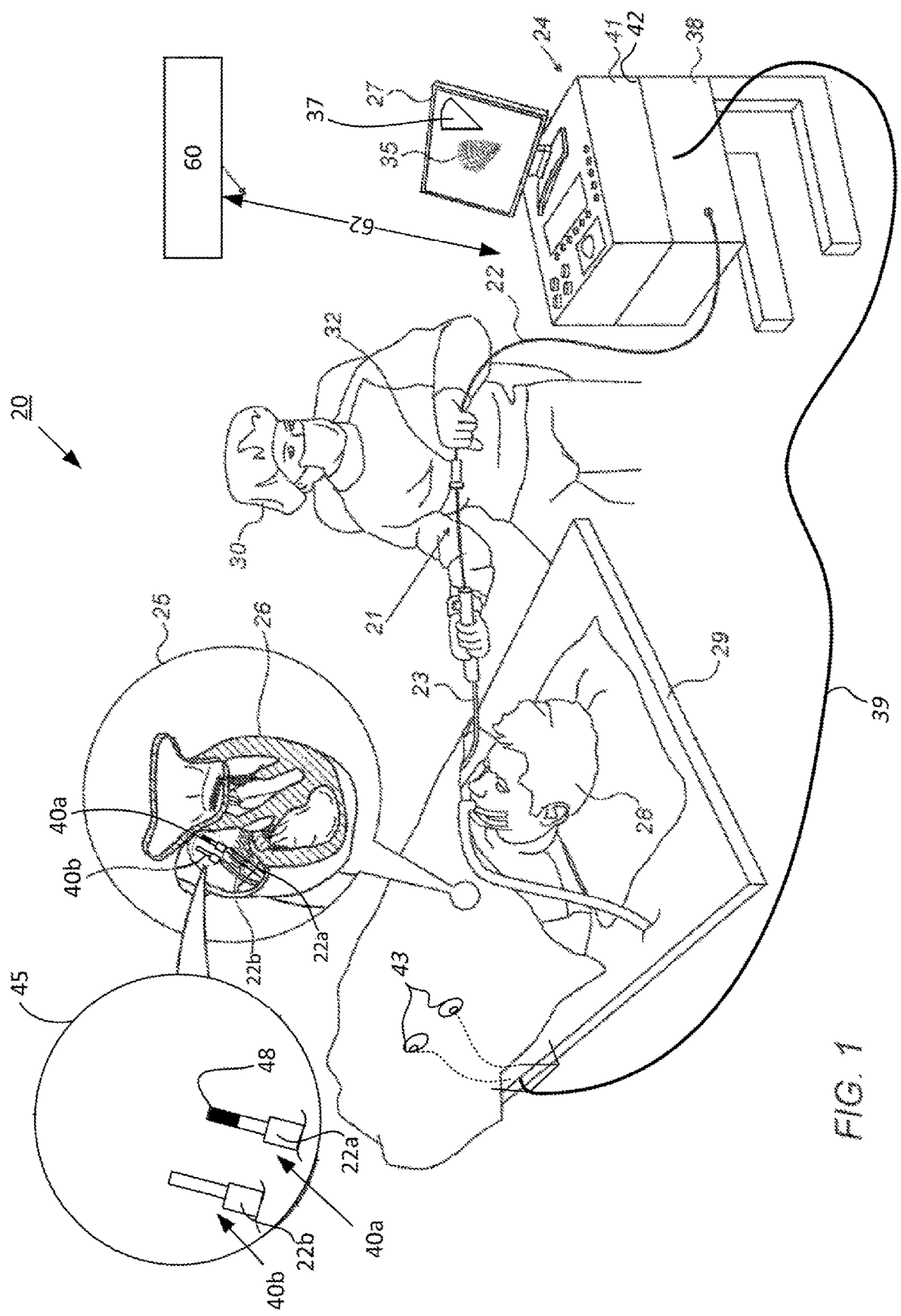
FIG. 1 is a diagram of an exemplary system in which one or more features of the disclosure subject matter can be implemented.

FIG. 1 is a diagram of an exemplary mapping system 20 in which one or more features of the disclosure subject matter can be implemented. Mapping system 20 may include devices, such as a catheter 40a and ultrasound transducer 40b, that are configured to obtain biometric data or ultrasound slices, in accordance with exemplary embodiments of the present invention. Although catheter 40a is shown to be a point catheter, it will be understood that a catheter of any shape that includes one or more elements (e.g., electrodes) may be used to implement the exemplary embodiments of the present invention. Mapping system 20 includes a probe 21, having shafts 22a and 22b that may be navigated by a medical professional 30 into a body part, such as heart 26, of a patient 28 lying on a bed 29. According to exemplary embodiments of the present invention, multiple probes may be provided such that a first probe is in connection with a catheter 40a and a different probe is in connection with ultrasound transducer 40b. However, for purposes of conciseness, a single probe 21 is described herein but it will be understood that probe 21 may represent multiple probes. As shown in FIG. 1, medical professional 30 may insert shaft 22a and/or 22b through a sheath 23, while manipulating the distal end of the shafts 22a and/or 22b using a manipulator 32 near the proximal end of the catheter 40a and/or ultrasound transducer 40b and/or deflection from the sheath 23. As shown in an inset 25, catheter 40a and/or ultrasound transducer 40b may be fitted at the distal end of shafts 22a and 22b respectively. Catheter 40a and/or ultrasound transducer 40*b* may be inserted through sheath 23 in a collapsed state and may be then expanded within heart 26.

According to exemplary embodiments of the present invention, ultrasound transducer 40*b* may be configured to obtain ultrasound slices of cardiac chamber of heart 26. Inset 45 shows the ultrasound transducer 40*b* in an enlarged view, inside a cardiac chamber of heart 26. As shown, ultrasound transducer 40*b* may be attached to shaft 22*b*.

According to exemplary embodiments of the present invention, catheter 40*a* may be configured to obtain biometric data of a cardiac chamber of heart 26. Inset 45 shows catheter 40*a* in an enlarged view, inside a cardiac chamber of heart 26. As shown, catheter 40 may include a point element 48 coupled onto the body of the catheter. According to other exemplary embodiments of the present invention, multiple elements may be connected via splines that form the shape of the catheter 40*a*. The element 48 may be any elements configured to obtain biometric data and may be electrodes, transducers, or one or more other elements.

According to exemplary embodiments of the present invention, biometric data may include one or more of LATS, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 1, the probe 21, ultrasound transducer 40*b*, and catheter 40*a* may be connected to a console 24. Console 24 may include a processor 41, such as a general-purpose computer, with suitable front end and interface circuits 38 for transmitting and receiving signals to and from catheter 40*a* and ultrasound transducer 40*b*, as well as for controlling the other components of mapping system 20. In some exemplary embodiments of the present invention, processor 41 may be further configured to receive biometric data and generate rendering data for a global view and local view, based on the biometric data, as further disclosed herein. According to exemplary embodiments of the present invention, the rendering data may be used to provide the medical professional 30 with a rendering of one or more body parts on a display 27, e.g., a body part rendering 35. According to an exemplary embodiment of the present invention, the processor may be external to the console 24 and may be located, for example, in the catheter, in an external device, in a mobile device, in a cloud-based device, or may be a standalone processor. According to exemplary embodiments of the present invention, the ultrasound transducer 40*b* may provide ultrasound slices which may be stored in memory 42, as further disclosed herein. The ultrasound transducer 40*b* may provide the ultrasound slices directly to memory 42 or the ultrasound slices maybe provided to processor 41 and the processor 41 may provide the ultrasound slices to memory 42.

As noted above, processor 41 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 1 may be modified to implement the exemplary embodiments of the present invention. The disclosed exemplary embodiments of the present invention may similarly be applied using other system components and settings. Additionally, mapping system 20 may include additional components, such as elements for sensing biometric patient data, wired or wireless connectors, processing and display devices, or the like.

According to an exemplary embodiment of the present invention, a display connected to a processor (e.g., processor 41) may be located at a remote location such as a separate hospital or in separate healthcare provider networks. Additionally, the mapping system 20 may be part of a surgical system that is configured to obtain anatomical and electrical measurements of a patient's organ, such as a heart, and performing a cardiac ablation procedure. An example of such a surgical system is the Carto® system sold by Biosense Webster.

The mapping system 20 may also, and optionally, obtain biometric data such as anatomical measurements of the patient's heart using ultrasound, computed tomography (CT), magnetic resonance imaging (MRI) or other medical imaging techniques known in the art. The mapping system 20 may obtain electrical measurements using catheters, electrocardiograms (EKGs) or other sensors that measure electrical properties of the heart. The biometric data including anatomical and electrical measurements may then be stored in a memory 42 of the mapping system 20, as shown in FIG. 1. The biometric data may be transmitted to the processor 41 from the memory 42. Alternatively, or in addition, the biometric data may be transmitted to a server 60, which may be local or remote, using a network 62. Similarly, ultrasound slices may be transmitted to a server 60, which may be local or remote, using a network 62.

Network 62 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 20 and the server 60. The network 62 may be wired, wireless or a combination thereof. Wired connections may be implemented using Ethernet, Universal Serial Bus (USB), RJ-11 or any other wired connection generally known in the art. Wireless connections may be implemented using WiMAX, and Bluetooth, infrared, cellular networks, satellite or any other wireless connection methodology generally known in the art. Additionally, several networks may work alone or in communication with each other to facilitate communication in the network 62.

In some instances, the server 60 may be implemented as a physical server. In other instances, server 60 may be implemented as a virtual server a public cloud computing provider (e.g., Amazon Web Services (AWS)®).

Control console 24 may be connected, by a cable 39, to body surface electrodes 43, which may include adhesive skin patches that are affixed to the patient 28. The processor, in conjunction with a current tracking module, may determine position coordinates of the catheter 40a and ultrasound transducer 40b inside the body part (e.g., heart 26) of a patient. The position coordinates may include the location and orientation of catheter 40a and ultrasound transducer 40b. The position coordinates may be based on impedances or electromagnetic fields measured between the body surface electrodes 43 and the electrode 48 or other electromagnetic components of the catheter 40a. Similarly, the position coordinates may be based on impedances or electromagnetic fields measured between the body surface electrodes 43 and the ultrasound transducer 40b. Additionally or alternatively, location pads may be located on the surface of bed 29 and may be separate from the bed 29. The position coordinates may be based on impedances or electromagnetic fields measured between the electrode 48 and/or a component of the ultrasound transducer 40b.

Processor 41 may comprise real-time noise reduction circuitry typically configured as a field programmable gate array (FPGA), followed by an analog-to-digital (A/D) ECG (electrocardiograph) or EMG (electromyogram) signal conversion integrated circuit. The processor 41 may pass the signal from an A/D ECG or EMG circuit to another processor and/or can be programmed to perform one or more functions disclosed herein.

Control console 24 may also include an input/output (I/O) communications interface that enables the control console to transfer signals from, and/or transfer signals to electrode 48 and/or ultrasound transducer 40b and electrodes 43 or a location pad. Based on signals received from electrode 48, ultrasound transducer 40b and/or electrodes 43, processor 41 may generate rendering data that enables a display, such as display 27 to render a body part, such as a body part rendering 35.

During a procedure, processor 41 may facilitate the presentation of a body part rendering 35 and/or an ultrasound slice 37 to medical professional 30 on a display 27, and store data representing the body part rendering 35 and ultrasound slice 37 in a memory 42. Memory 42 may comprise any suitable volatile and/or non-volatile memory, such as random-access memory or a hard disk drive. In some exemplary embodiments of the present invention, medical professional 30 may be able to manipulate a body part rendering 35 and/or ultrasound slice 37 using one or more input devices such as a touch pad, a mouse, a keyboard, a gesture recognition apparatus, or the like. For example, an input device may be used to change the position of catheter 40a such that rendering 35 is updated and a different ultrasound slice 37 is provided based on the updated position, as disclosed herein. In alternative exemplary embodiments of the present invention, display 27 may include a touchscreen that can be configured to accept inputs from medical professional 30, in addition to presenting a body part rendering 35 and ultrasound 37, including a global view and a local view.

According to exemplary embodiments of the present invention, an ultrasound transducer may be configured to capture ultrasound slices at various positions within the intra-body organ. The ultrasound transducer may be the same as or similar to ultrasound transducer 40b of FIG. 1. The ultrasound transducer may be inserted into an intra-body organ, such as a heart 26 of FIG. 1. More specifically, the ultrasound transducer may be inserted into a chamber of in intra-body organ, such as a heart chamber of heart 26. The ultrasound transducer may be configured to automatically capture ultrasound slices at pre-determined intervals of time (e.g., one ultrasound slice per millisecond) or may be configured to capture ultrasound slices based on the position and/or movement of the ultrasound transducer. For example, the ultrasound transducer may be configured to capture up to a given number of ultrasound slices (e.g., three ultrasound slices) per each position of the ultrasound transducer. Accordingly, the ultrasound transducer may be configured to capture multiple ultrasound slices for each ultrasound transducer position. According to an exemplary embodiments of the present invention, a processor, such as processor 41 of FIG. 1, maybe configured to select a single ultrasound slice from a plurality of ultrasound slices at the same ultrasound position. The processor may select the single ultrasound slice based one or more factors such as ultrasound slice quality, ultrasound transducer stability while the ultrasound slice is collected, signal to noise ratio, or the like. As an example, an ultrasound slice quality may be determined based on the detected boundaries of the organ within the slice when compared to free space (e.g., a blood pool) of the organ within the slice. A first ultrasound slice may be replaced by a second ultrasound for the same ultrasound position, based on the selection and factors described herein.

As applied herein, an ultrasound position may correspond to either an ultrasound transducer position or an ultrasound slice position, as further described herein. An ultrasound transducer position may be the position of an ultrasound transducer when a given ultrasound slice is captured. The ultrasound transducer position may include an ultrasound transducer location (e.g., coordinates) and an ultrasound transducer orientation (e.g., angle), as further disclosed herein. The ultrasound slice position may correspond to the area, volume, or voxels occupied by the ultrasound slice. As applied herein, a catheter position may correspond to either a catheter location (e.g., coordinates) and orientation (e.g., angle) or may correspond to a catheter slice position, as further disclosed herein.

According to an exemplary embodiment of the present invention, an ultrasound transducer position or a catheter position may include both the location and orientation of the corresponding ultrasound transducer or catheter. A location (i.e., ultrasound transducer position or a catheter position) may be stored as or include coordinates which may be represented as cartesian coordinates, polar coordinates, voxel coordinates, or any other applicable coordinates or a combination thereof. The location may be relative to a reference point which may be internal to the body, internal to an intra-body organ, internal to an intra-body organ chamber or external to the body. The location may be determined based on signals (e.g., electromagnetic signals) from the ultrasound transducer, the catheter, body surface electrodes (e.g., body surface electrodes 43 of FIG. 1), a location pad, or other location-based component.

An orientation may be based on a reference point (e.g., tip) of the ultrasound transducer or catheter such that the orientation indicates the direction that the reference point of the ultrasound transducer and/or catheter is facing. It will be understood that although a reference point is specifically recited herein, the reference point may be a collection of points, such as a line. The reference point may be any part of an ultrasound transducer or catheter such as a distal point, a proximal point, or any other applicable point. The orientation may be stored or include an angle, a phase, a direction, an axis, an elevation, or a combination thereof.

Figure 2:
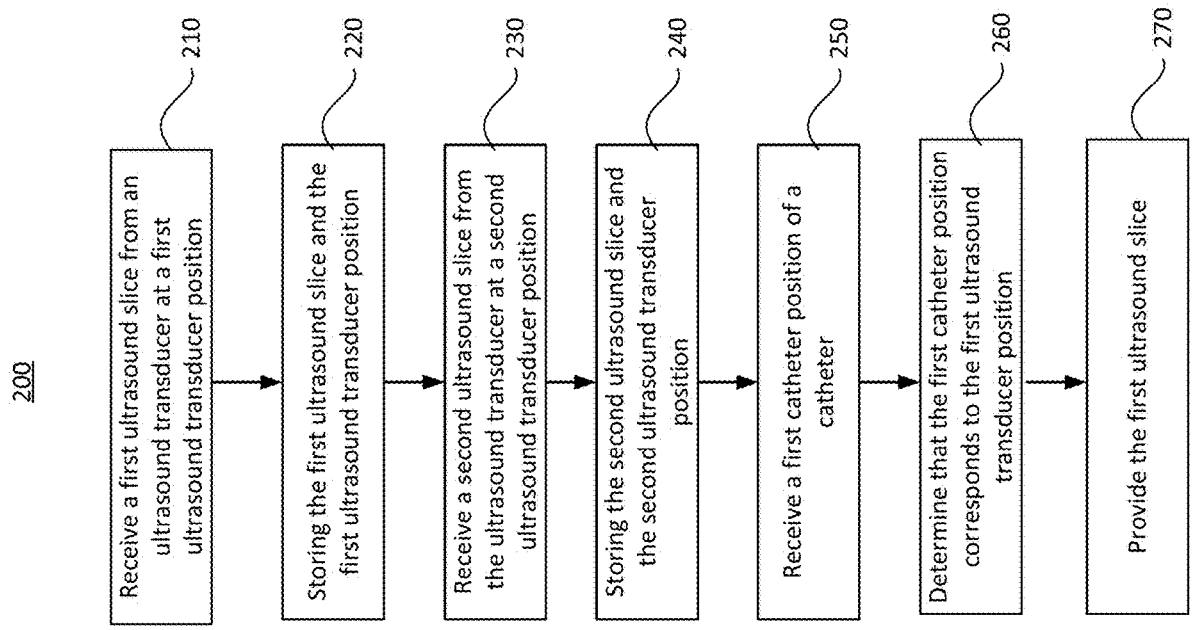
FIG. 2 is a flowchart for providing an ultrasound slice based on a catheter's position.

FIG. 2 shows a process flowchart 200 for providing a previously stored ultrasound slice, from a plurality of previously stored ultrasound slices, based on a catheter's position.

At step 210 of the process illustrated in FIG. 2, a first ultrasound slice may be received from an ultrasound transducer while the ultrasound transducer is in a first ultrasound transducer position. The first ultrasound slice captured while the ultrasound transducer is in a first position may be one of a plurality of slices that are collected while the ultrasound transducer is in the first position. As disclosed herein, a processor may designate a single ultrasound slice from the plurality of ultrasound slices as the first ultrasound slice for a given ultrasound location, based on one or more of ultrasound slice quality, ultrasound transducer stability while the ultrasound slice is collected, signal to noise ratio, or the like.

Figure 3A:
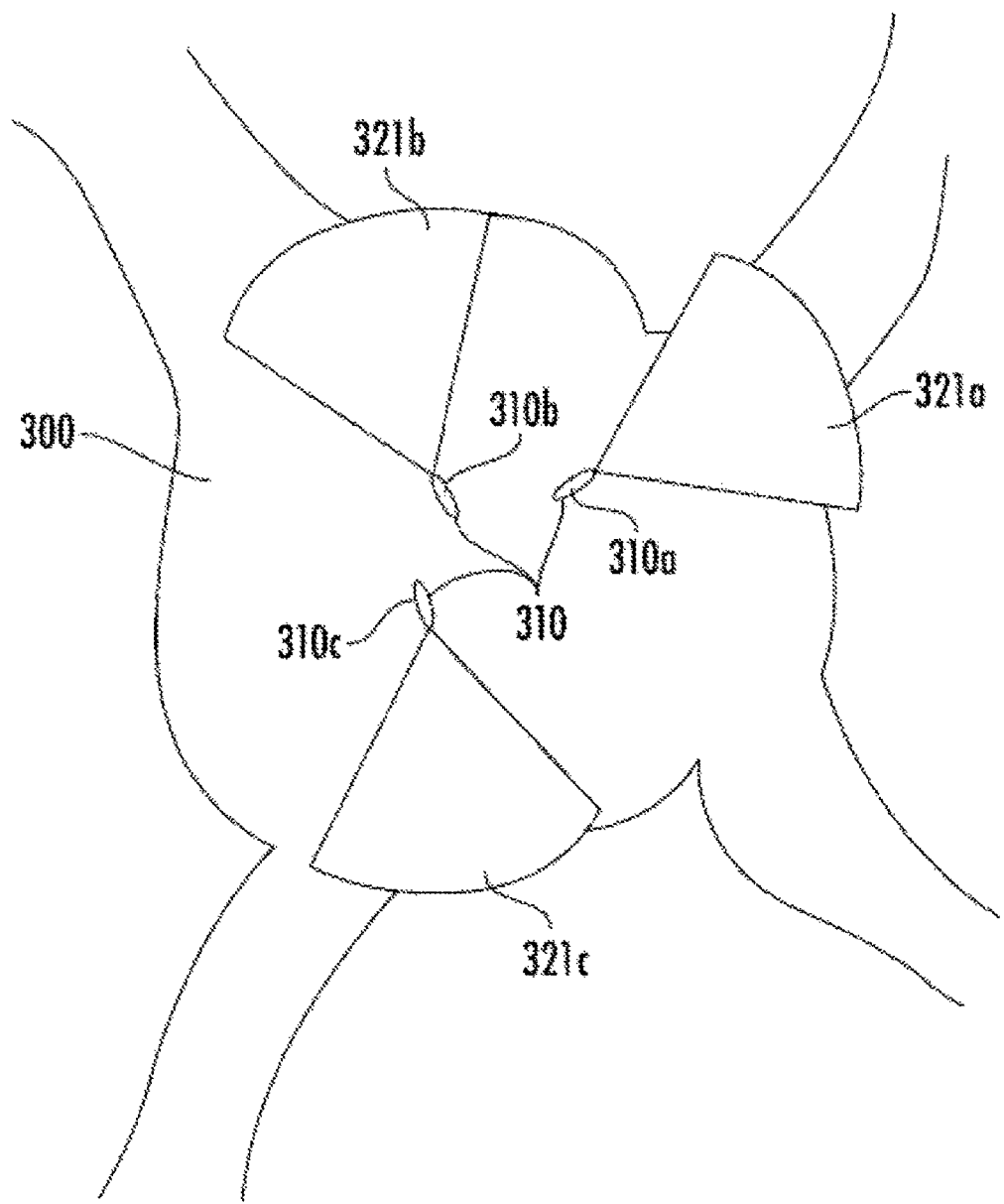
FIG. 3A is an illustration of an ultrasound transducer collecting ultrasound slices at various positions.

FIG. 3A shows an example diagram of a heart chamber 300 with an ultrasound transducer 310 in a plurality of positions 310a, 310b, and 310c. As shown in FIG. 3A, and in accordance with step 210 of the process illustrated in FIG. 2, a first ultrasound slice 321a may be received from the ultrasound transducer 310 while the ultrasound transducer is in a first ultrasound transducer position 310a. The first ultrasound transducer position 310a may be represented by a location (e.g., coordinates) as well as an orientation (e.g., an angle and elevation) such that slice 321a is associated with the first ultrasound transducer position 310a.

At step 220 of the process illustrated in FIG. 2, the first ultrasound slice and the first ultrasound transducer position corresponding to the first ultrasound slice may be stored in any applicable storage medium such as in a memory 42 of FIG. 1. The first ultrasound slice may be stored as an image type file, a video type file, or any other file that enables the first ultrasound slice to be rendered at a time after the first ultrasound slice is captured by the ultrasound transducer. The first ultrasound transducer position may be stored within the same file or group of files that include the first ultrasound slice or may be stored in a separate memory location than the first ultrasound slice such that the stored first ultrasound transducer position and the first ultrasound slice are correlated to each other through any applicable manner such as via a pointer, a lookup table, or the like. In accordance with the example provided in FIG. 3A, the first ultrasound slice 321a and the first ultrasound transducer position 310a may be stored in a memory.

At step 230 of the process illustrated in FIG. 2, a second ultrasound slice may be received from an ultrasound transducer while the ultrasound transducer is in a second ultrasound transducer position. The second ultrasound slice captured while the ultrasound transducer is in a second position may be one of a plurality of slices that are collected while the ultrasound transducer is in the second position, as disclosed herein. A single slice from the plurality of slices collected while the ultrasound transducer is in the second position may be designated as the second ultrasound slice. As shown in FIG. 3A, and in accordance with step 230 of the process illustrated in FIG. 2, a second ultrasound slice 321b may be received from the ultrasound transducer 310 while the ultrasound transducer is in a second ultrasound transducer position 310b. The second ultrasound transducer position 310b may be represented by a location (e.g., coordinates) as well as an orientation (e.g., an angle and elevation) such that slice 321b is associated with the second ultrasound transducer position 310b.

At step 240 of the process illustrated in FIG. 2, the second ultrasound slice and the second ultrasound transducer position corresponding to the second ultrasound slice may be stored in any applicable storage medium such as in a memory 42 of FIG. 1 in a similar manner as that disclosed in accordance with step 220. Although steps 210 through 240 disclose a first ultrasound slice and a second ultrasound slice for simplicity, it will be understood that one or more additional ultrasound slices may be captured and stored. For example, as shown in FIG. 3A, ultrasound slice 321c may be captured while the ultrasound transducer 310 is in an ultrasound transducer position 310c and the corresponding data may be stored in a memory.

At step 250 of the process illustrated in FIG. 2, a first catheter position corresponding to an intra-body catheter may be received. The intra-body catheter may be the same as or similar to the catheter 40a of FIG. 1 and may be inserted into an intra-body chamber either while an ultrasound transducer is in the intra-body chamber or after an ultrasound transducer is removed from the intra-body chamber. The first catheter position may be received via any applicable means including via electromagnetic signals between electrodes on the catheter and a location pad, electromagnetic signals between electrodes on the catheter and body electrodes, etc. The first catheter position may include a location and an orientation, as disclosed herein. According to an implementation of this exemplary embodiment, the first catheter position may be in the same format as the ultrasound transducer positions stored at steps 220 and 240 of FIG. 2. According to another implementation, the first catheter position may be in a different format than the ultrasound transducer positions stored at steps 220 and 240 but may be converted such that they can be correlated with the format of the ultrasound transducer positions stored at steps 220 and 240.

Figure 3B:
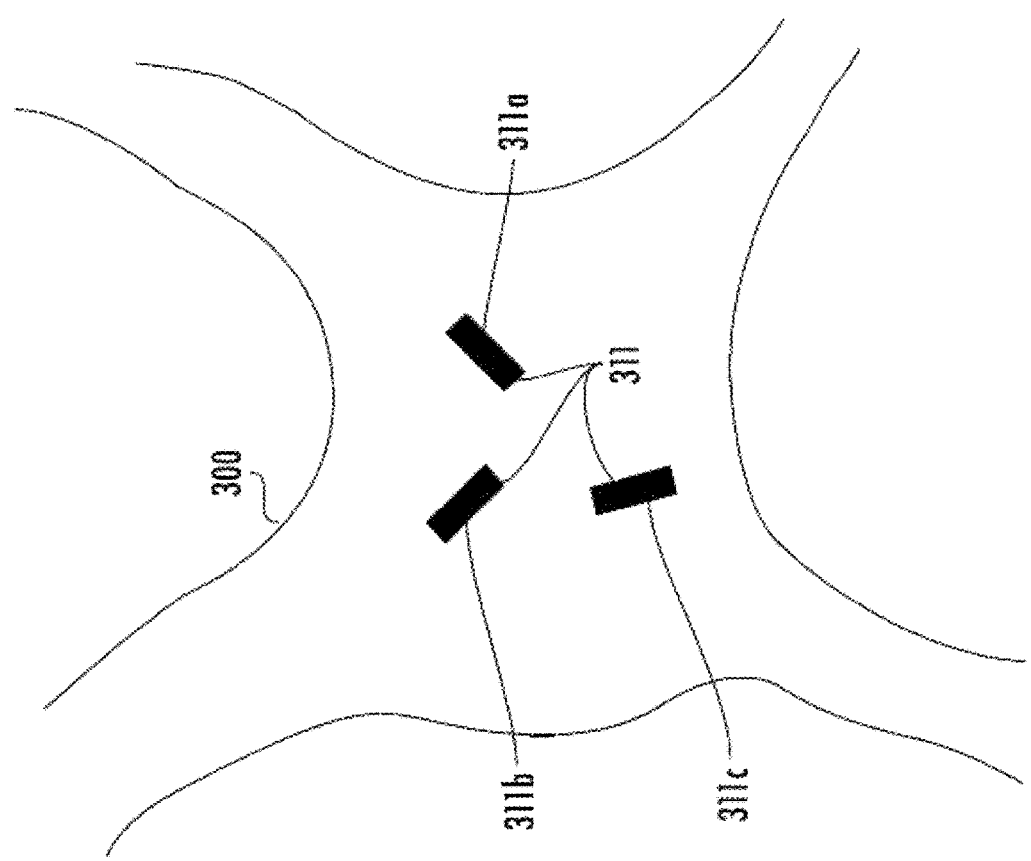
FIG. 3B is an illustration of a catheter at various positions corresponding to the positions of FIG. 3A.

FIG. 3B shows an example diagram of the heart chamber 300 of FIG. 3A with a catheter 311 at various positions 311a, 311b, and 311c. As shown in FIG. 3B, and in accordance with step 250 of the process illustrated in FIG. 2, the catheter's position while the catheter is in the first position 311a may be received. The catheter's position may be updated at pre-determined time intervals or based on detection of movement of the catheter.

At step 260 of the process illustrated in FIG. 2, a determination may be made that the first catheter position received at step 250 corresponds to the first ultrasound transducer position received at step 210 and stored at 220. Although the first catheter position received at step 250 is described as corresponding to the first ultrasound transducer position received at step 210 for simplicity, it will be understood that a catheter position may correspond to any one of the ultrasound transducer position.

The determination that the first catheter position received at step 250 corresponds to the first ultrasound transducer position may be based on comparing the received catheter position (i.e., step 250) to the stored ultrasound transducer positions (i.e., steps 220 and 240). According to an exemplary embodiment of the present invention, the catheter position may be received in the same format as the stored ultrasound transducer positions. For example, the catheter position may include the catheter location which may be received as a set of coordinates and may also include the catheter orientation which may be received as an angle and an elevation. For example, the catheter position may include a location x, y, and z coordinates (4 mm, 8 mm, 1 mm) from a coordinate reference point such as an external patch or an area within an intra-body organ. The catheter position may include an angle 44 degrees corresponding to the horizontal angle of a reference point (e.g., tip) of the catheter and an elevation of 14 degrees corresponding to the vertical angle of the reference point of the catheter. According to this example, the catheter position may be represented as (4, 8, 1, 44, 14). At step 260, the catheter position may be compared to a plurality of ultrasound transducer positions which may be in the same format. For example, the first ultrasound transducer position stored at step 220 may be (5, 8, 1, 44, 14) and the second ultrasound transducer position stored at step 240 may be (6, 8, 1, 44, 14). A calculation may be made as to which of the plurality of stored ultrasound transducer positions is the closest to the received catheter position. Continuing the example, since the catheter position (4, 8, 1, 44, 14) is only 1 mm different than the first ultrasound transducer position (5, 8, 1, 44, 14), it may be determined the first ultrasound transducer position corresponds to the catheter position as the second ultrasound transducer position (6, 8, 1, 44, 14) is 2 mm different than the catheter position.

According to an exemplary embodiment of the present invention, the received catheter position may be in a different format (e.g., polar coordinates instead of cartesian coordinate than the plurality of stored ultrasound transducer positions. It will be understood that one or more of the different formats may be converted such that both sets of positions (catheter positions and ultrasound transducer positions) may be compared to each other to determine which of a plurality of ultrasound transducer positions corresponds to the catheter position.

According to an exemplary embodiment of the present invention, a correlation threshold may be provided such that if the differences between a catheter position and all available ultrasound transducer positions are greater than the correlation threshold then a determination is made that no ultrasound transducer position corresponds to the catheter position. Accordingly, at step 270, as further disclosed herein, no ultrasound slice may be displayed. Notably, in this scenario, there may be no ultrasound slices that would visually show the area that corresponds to a current catheter position and, thus, no ultrasound slice may be provided at step 270.

At step 270 of the process illustrated in FIG. 2, the ultrasound slice (e.g., first ultrasound slice) associated with the ultrasound transducer position (e.g., first ultrasound transducer position) that is determined to correspond to the catheter position, at step 260, may be provided. The ultrasound slice may be provided via a display such as display 27 of FIG. 1. Alternatively, the ultrasound slice may be provided to an external display such as via network 62 and server 60 such that the ultrasound slice may be displayed at a remote location.

According to another exemplary embodiment of the present invention, as shown via process 400 of FIG. 4, a previously stored ultrasound slice may be provided selected based on a catheter's position corresponding to the ultrasound slice's position. At step 410 of the process illustrated in FIG. 4, a first ultrasound slice with a corresponding first ultrasound slice position may be received from an ultrasound transducer.

An ultrasound slice position may correspond to the voxels that are occupied by an ultrasound slice. A voxel may be a value on a grid in three-dimensional space such as the three-dimensional space occupied by the interior of an intra-body chamber, such as a chamber within a heart. A mapping system, such as mapping system 20 of FIG. 1 may infer the position of a voxel based upon its position relative to other voxels within the same three-dimensional space. According to this exemplary embodiment of the present invention, an ultrasound slice position may correspond to the voxels that intersect with the ultrasound slice. To clarify, an ultrasound slice may capture an area form within an intra-body chamber. The area captured by the ultrasound slice may intersect a plurality of voxels within the intra-body chamber. Each of the voxels may correspond to a value or location such that each voxel is distinguished in space from all the other voxels within that space. According to an exemplary embodiment of the present invention, all voxels that intersect with an ultrasound slice may comprise the location of the ultrasound slice itself. According to another exemplary embodiment of the present invention, all voxels that have at least one dimension fully encompassed by an ultrasound slice may comprise the location of the ultrasound slice itself.

Figure 5A:
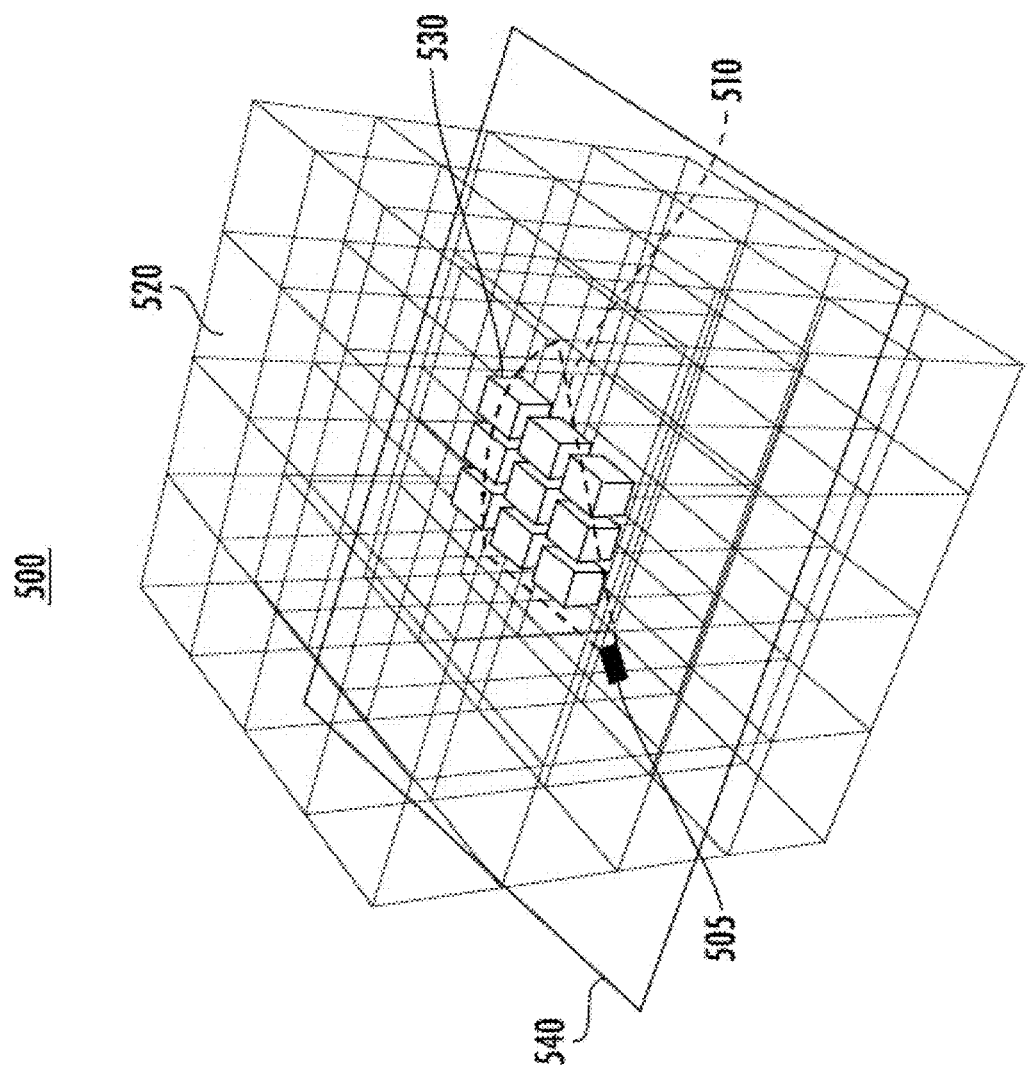
FIG. 5A is a diagram that shows an ultrasound slice intersecting with voxels in a three-dimensional space.

FIG. 5A shows a three-dimensional space 500 with a plurality of voxels 520 arranged in a grid pattern. It will be understood that although the three-dimensional space 500 is shown as a rectangular prism for simplicity, exemplary embodiments disclosed herein may be implemented with any applicable three-dimensional space such as the shape of an intra-body chamber. As shown in FIG. 5A, the location of ultrasound slice 510 captured by ultrasound transducer 505 may be defined by the highlighted voxels 530. The highlighted voxels 530 shown in FIG. 5A correspond to all voxels that the ultrasound slice 510 intersects with such that if an edge of the ultrasound slice 510 intersects with any part of the voxel, then the entire voxel is applied when defining the location of the ultrasound slice.

According to another exemplary embodiment of the present invention that is not shown, a voxel may be applied when defining the location of an ultrasound slice only if at least one full dimension of the voxel is within the area occupied by an ultrasound slice.

Figure 5C:
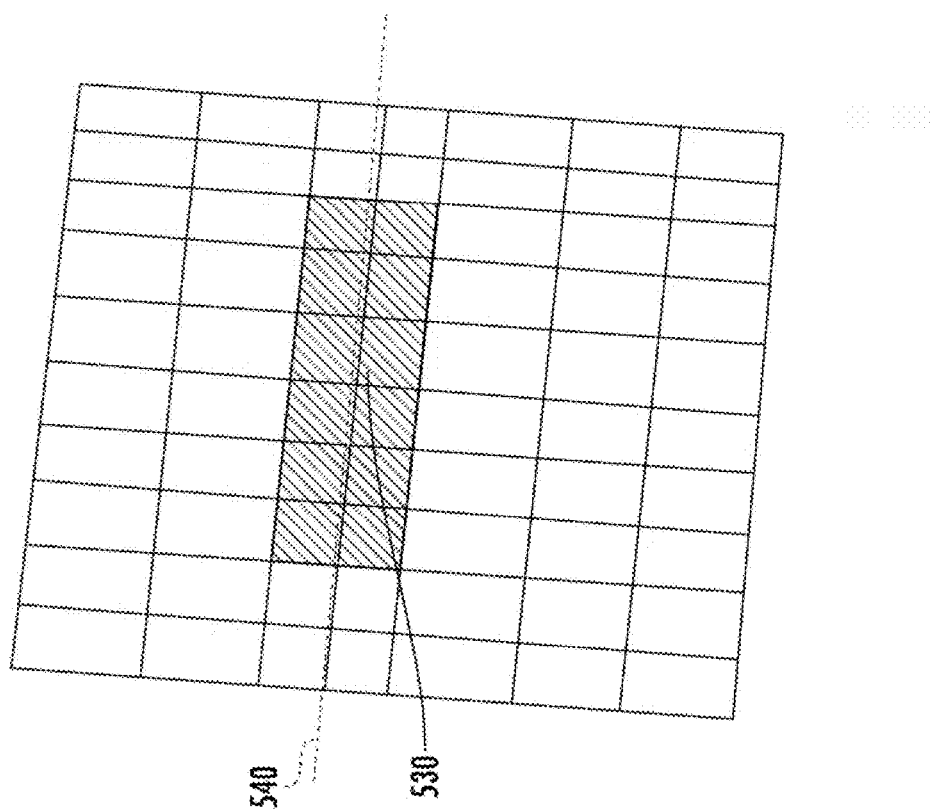
FIG. 5C is a vertical cross-section of FIG. 5A.
Figure 5B:
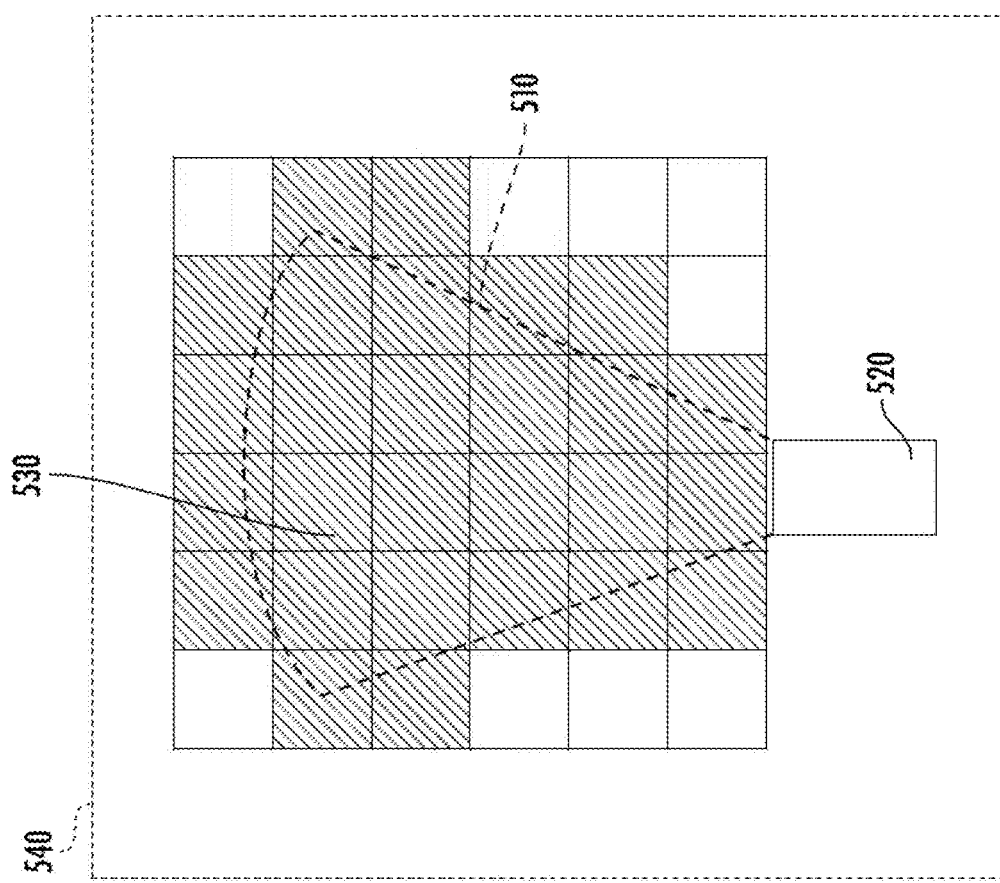
FIG. 5B is a horizontal cross-section of FIG. 5A.

FIG. 5B shows a horizontal cross section of FIG. 5A. The horizontal cross section shown in FIG. 5B corresponds to the horizontal plane 540 of FIG. 5A which is also reproduced in FIG. 5B. As shown in FIG. 5B, the highlighted voxels 530 correspond to the voxels that intersect with the ultrasound slice 510. According to this example, the ultrasound slice 510 may be contained within the same horizontal plane 540 such that the angle of the ultrasound transducer while capturing ultrasound slice 540 may be 0. Accordingly, FIG. 5B shows a the horizontal plane 540 that includes an intersection with each of the highlighted voxels 530. It will be understood that an ultrasound slice may span a plurality of planes such that a single horizontal plane may not capture each of the intersecting voxels.

FIG. 5C shows a vertical cross section of FIG. 5A which includes the highlighted voxels 530 that intersect with the ultrasound slice 510 (not shown). For reference the horizontal plane 540 is shown as it would intersect with the voxels provided within the three-dimensional space 500.

At step 420 of the process illustrated in FIG. 4, the first ultrasound slice and the first ultrasound slice position may be stored in a memory such as memory 42 of FIG. 1. The first ultrasound slice may be stored as an image type file, a video type file, or any other file that enables the first ultrasound slice to be rendered at a time after the first ultrasound slice is captured by the ultrasound transducer. The first ultrasound slice position may be stored within the same file or group of files that include the first ultrasound slice or may be stored in a separate memory location than the first ultrasound slice such that the stored first ultrasound slice position and the first ultrasound slice are correlated to each other through any applicable manner such as via a pointer, a lookup table, or the like. In accordance with the example provide in FIG. 5A, the ultrasound slice 510 may be stored in a memory and the ultrasound slice 510 may be associated with a stored location of the highlighted voxels 530.

At step 430 of the process illustrated in FIG. 4, a second ultrasound slice with a corresponding second ultrasound slice position may be received from the ultrasound transducer. The second ultrasound slice position may be defined by a different set of voxels than the first ultrasound slice position as the second ultrasound slice may be captured while the ultrasound transducer is in a different position than when the first ultrasound slice was captured by the ultrasound transducer, as described for step 410.

At step 440 of the process illustrated in FIG. 4, the second ultrasound slice and the second ultrasound slice position corresponding to the second ultrasound slice may be stored in any applicable storage medium such as in a memory 42 of FIG. 1 in a similar manner as that disclosed in accordance with step 420. Although steps 410 through 440 disclose a first ultrasound slice and a second ultrasound slice for simplicity, it will be understood that one or more additional ultrasound slices may be captured and stored.

Figure 6:
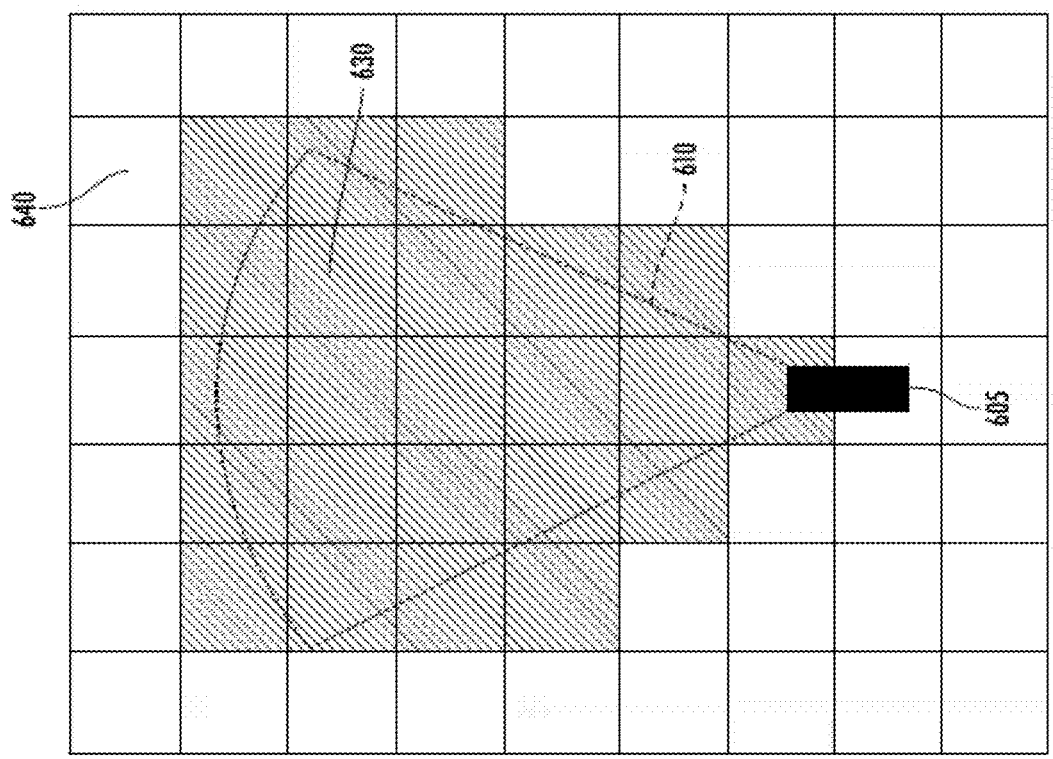
FIG. 6 is a diagram of a catheter slice based on an imaginary fan.

At step 450 of the process illustrated in FIG. 4, a first catheter position corresponding to an intra-body catheter may be received and the catheter position may be a catheter slice. A catheter slice may be determined based on an "imaginary fan" that originates from the catheter's location in the direction that the catheter is facing. The catheter slice may be designated by the voxels that intersect the imaginary fan in a manner similar to that of determining an ultrasound slice position, as disclosed herein. The imaginary fan may be similar to an ultrasound slice such that the imaginary fan may occupy a similar shape as an ultrasound slice if the catheter were an ultrasound transducer. FIG. 6 shows a two-dimensional example of an imaginary fan 610 generated based on a catheter 605. As shown in FIG. 6, the intersecting voxels 630 may correspond to the voxels that intersect the imaginary fan 610. As shown, non-intersecting voxels 640 correspond to voxels that do not intersect with the imaginary fan 610. The intersecting voxels 630 may be designated as the catheter slice and may indicate the catheter position of the catheter.

The intersecting voxels that designate the catheter slice may be determined via any applicable manner including based on electromagnetic signals between electrodes on the catheter and a location pad, electromagnetic signals between electrodes on the catheter and body electrodes, etc. According to an implementation of this exemplary embodiment, the catheter position (i.e., the catheter slice) may be provided in the same format as the ultrasound slice positions stored at steps 420 and 440 (e.g., by designating intersecting voxels). According to another implementation, the catheter position may be in a different format as the ultrasound slice positions stored at steps 420 and 440 but may be converted such that they can be correlated with the format of the ultrasound slice positions stored at steps 420 and 440.

At step 460 of the process illustrated in FIG. 4, a determination may be made that the first catheter position received at step 450 corresponds to the first ultrasound slice position received at step 410 and stored at 420. Although the first catheter position received at step 450 is described as corresponding to the first ultrasound slice position received at step 410 for simplicity, it will be understood that a catheter position may correspond to any one of a plurality of ultrasound slice positions.

The determination that the catheter slice position received at step 450 corresponds to the first ultrasound slice position may be based on comparing the received catheter slice position (i.e., step 450) to the stored ultrasound slice positions (i.e., steps 420 and 440).

According to an exemplary embodiment of the present invention, a catheter position may be received and may include a catheter location a catheter orientation. Based on the catheter location and catheter orientation, an imaginary fan may be determined, in accordance with the example provided in FIG. 6. Each voxel within a three-dimensional space may be initiated with a voxel value of 0. The voxel value for each voxel within the three-dimensional space that intersects with the imaginary fan may be incremented by a value of 1 such that each such intersecting voxel may have a voxel value of 1. Thereafter, the voxels that intersect with the stored first ultrasound slice at step 420 may be designated a voxel value of 1, and the intersecting voxels from the stored first ultrasound slice at step 420 may be overlaid onto the imaginary fan such that any voxels that intersect with both the imaginary fan and the first ultrasound slice are incremented by another value of 1. Accordingly, the voxels that intersect with both the imaginary fan and the first ultrasound slice may have a first voxel value of 2.

The same process may be applied to the stored second ultrasound slice at step 440 such that the voxels that intersect with the stored second ultrasound slice at step 440 may be designated a voxel value of 1, and the intersecting voxels from the stored second ultrasound slice at step 440 may be overlaid onto the imaginary fan such that any voxels that intersect with both the imaginary fan and the second ultrasound slice are incremented by another value of 1. Accordingly, the voxels that intersect with both the imaginary fan and the second ultrasound slice may have a second voxel value of 2. This process may be repeated for each stored ultrasound slice. The ultrasound slice that results in the most number of voxels with a voxel value of 2 may be determined to correspond to the catheter slice position. Notably, the ultrasound slice that results in the most number of voxels with a voxel value of 2 may be the ultrasound slice that was captured when the ultrasound transducer was in a position that is closest in location and orientation to the catheter. According to the process 400 illustrated in FIG. 4, the first ultrasound slice may be determined to correspond to the catheter slice position based on the first ultrasound slice having the most number of voxels with a voxel value of 2.

At step 470 of the process illustrated in FIG. 4, the first ultrasound slice may be provided for display based on determining that the first ultrasound slice corresponds to the catheter slice position.

It will be understood that although ultrasound slices and imaginary fans are disclosed herein as two-dimensional slices and fans, that the ultrasound slices and/or the imaginary fans may be three dimensional.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A method for displaying information to a surgeon at a time a catheter is inserted into a patient, the method comprising:
    sending first electromagnetic signals to an ultrasound transducer;
    receiving, based on the first electromagnetic signals, a first ultrasound slice from the ultrasound transducer during a first time period, the first ultrasound slice corresponding to a first ultrasound position including at least first coordinates of the ultrasound transducer, wherein the first coordinates are a first location on an x-axis, a y-axis and a z-axis relative to a first reference point;
    sending second electromagnetic signals to the ultrasound transducer;
    receiving, based on the second electromagnetic signals, a second ultrasound slice from the ultrasound transducer during a second time period, the second ultrasound slice corresponding to a second ultrasound position including at least second coordinates of the ultrasound transducer, wherein the second coordinates are a second location on the x-axis, the y-axis and the z-axis relative to the first reference point;
    storing the first ultrasound slice and the second ultrasound slice;
    determining, a first catheter position of the catheter in first catheter coordinates at a third time period, wherein the first catheter coordinates are relative to a second reference point and the third time period is subsequent to the first time period and the second time period;
    selecting either the first ultrasound slice or the second ultrasound slice as a selected slice by comparing the first catheter position, the first ultrasound position, and the second ultrasound position, wherein the first ultrasound slice is selected as the selected slice when the comparing indicates that the first catheter position is closer to the first ultrasound position and the second ultrasound slice is selected as the selected slice when the comparing indicates that the first catheter position is closer to the second ultrasound position;
    determining a live location of the catheter relative to the selected slice; and
    displaying the live location of the catheter and the selected slice as the information to the surgeon.

2. The method of claim 1, wherein the first ultrasound position is one of an ultrasound transducer position or an ultrasound slice position and the first catheter position comprises at least one of a catheter orientation, or a catheter slice.

3. The method of claim 2, wherein determining that the first catheter position is closer to the first ultrasound position than the second ultrasound position comprises determining that the catheter slice intersects with the first ultrasound slice more than the catheter slice intersects with the second ultrasound slice.

4. The method of claim 2, wherein determining that the first catheter position corresponds to the first ultrasound position further comprises:
    determining a first set of voxels that intersect the catheter slice;
    determining a first number of voxels, from the first set of voxels, that intersect with the first ultrasound slice;
    determining a second number of voxels, from the first set of voxels, that intersect with the second ultrasound slice; and
    determining that the first number of voxels is greater than the second number of voxels.

5. The method of claim 1, wherein the first ultrasound position and/or the second ultrasound position comprises at least one of an ultrasound transducer location or an ultrasound transducer orientation.

6. The method of claim 1, further comprising
    moving the catheter from the first catheter position to a second catheter position, wherein the second catheter position is closer to the second ultrasound position than the first ultrasound position; and
    selecting the second ultrasound slice as the selected slice after moving the catheter.

7. The method of claim 1, further comprising replacing the first ultrasound slice stored with an updated first ultrasound slice.

8. The method of claim 7, wherein the updated first ultrasound slice is received after receiving the first ultrasound slice.

9. A system for displaying information to a surgeon at a time a catheter is inserted into a patient, the system comprising:
    an ultrasound transducer configured to:
    receive first electromagnetic signals,
    capture, based on the first electromagnetic signals, a first ultrasound slice during a first time period, the first ultrasound slice corresponding to a first ultrasound position including at least first coordinates of the ultrasound transducer, wherein the first coordinates are a first location on an x-axis, a y-axis and a z-axis relative to a reference point,
    receive second electromagnetic signals, and
    capture, based on the second electromagnetic signals, a second ultrasound slice during a second time period, the second ultrasound slice corresponding to a second ultrasound position including at least second coordinates of the ultrasound transducer, wherein the second coordinates are a second location on the x-axis, the y-axis and the z-axis relative to the reference point;
    a memory, wherein the memory is configured to store the first ultrasound slice and the second ultrasound slice; and
    one or more processors that are communicatively coupled to the memory, and the ultrasound transducer, wherein the one or more processors are collectively configured to:
    determine a first catheter position of the catheter in first catheter coordinates at a third time period, wherein the first catheter coordinates are relative to a second reference point and the third time period is subsequent to the first time period and the second time period, select either the first ultrasound slice or the second ultrasound slice as a selected slice by comparing the first catheter position, the first ultrasound position, and the second ultrasound position, wherein the first ultrasound slice is selected as the selected slice when the comparing indicates that the first catheter position is closer to the first ultrasound position and the second ultrasound slice is selected as the selected slice when the comparing indicates that the first catheter position is closer to the second ultrasound position, determine a live location of the catheter relative to the selected slice, and display the live location of the catheter and the selected slice as the information to the surgeon.

10. The system of claim 9, wherein determining that the first catheter position is closer to the first ultrasound position than the second ultrasound position comprises determining that a catheter slice corresponding to the first catheter position intersects with the first ultrasound slice more than the catheter slice intersects with the second ultrasound slice.

11. The system of claim 9, wherein the first ultrasound position comprises at least one of an ultrasound transducer location and an ultrasound transducer orientation.

12. The system of claim 9, further comprising a location pad and determining at least one of the first ultrasound position, the second ultrasound position, and the first catheter position based on the location pad.

13. The system of claim 9, wherein determining that the first catheter position corresponds to the first ultrasound position comprises:

determining a first set of voxels that intersect a catheter slice corresponding to the first catheter position;

determining a first number of voxels, from the first set of voxels, that intersect with the first ultrasound slice;

determining a second number of voxels, from the first set of voxels, that intersect with the second ultrasound slice; and determining that the first number of voxels is greater than the second number of voxels.

* * * * *

UNITED STATES PATENT AND TRADEMARK OFFICE
CERTIFICATE OF CORRECTION

PATENT NO. : 12,263,033 B2  
APPLICATION NO. : 16/681408  
DATED : April 1, 2025  
INVENTOR(S) : Tamir Avraham Yellin et al.

Page 1 of 1

It is certified that error appears in the above-identified patent and that said Letters Patent is hereby corrected as shown below:

In the Specification

In Column 1, Line 65, delete "space." and insert -- space; --, therefor.
In Column 3, Line 23, delete "LATS," and insert -- LATs, --, therefor.
In Column 4, Line 56, delete "WiMAX," and insert -- Wi-Fi, WiMAX, --, therefor.
In Column 4, Line 63, delete "server" and insert -- server by --, therefor.
In Column 5, Line 64, delete "in" and insert -- an --, therefor.
In Column 6, Line 14, delete "based" and insert -- based on --, therefor.
In Column 9, Line 17, delete "(e.g.," and insert -- e.g., --, therefor.
In Column 9, Line 66, delete "form" and insert -- from --, therefor.
In Column 10, Line 40, delete "a the" and insert -- a --, therefor.
In Column 10, Line 64, delete "provide" and insert -- provided --, therefor.

In the Claims

In Column 14, Line 26, in Claim 6, delete "comprising" and insert -- comprising: --, therefor.

Signed and Sealed this  
Twenty-seventh Day of May, 2025

Coke Morgan Stewart  
*Acting Director of the United States Patent and Trademark Office*